(12) United States Patent
Schultz

(10) Patent No.: US 8,708,985 B2
(45) Date of Patent: Apr. 29, 2014

(54) SYSTEMS AND METHODS FOR EVACUATING MATERIALS AT A SURGICAL SITE

(75) Inventor: Leonard S. Schultz, Bloomington, MN (US)

(73) Assignee: Nascent Surgical, LLC, Eden Prairie, MN (US)

( * ) Notice: Subject to any disclaimer, the term of this patent is extended or adjusted under 35 U.S.C. 154(b) by 47 days.

(21) Appl. No.: 13/091,213

(22) Filed: Apr. 21, 2011

(65) Prior Publication Data

US 2012/0271253 A1  Oct. 25, 2012

(51) Int. Cl.
*A61M 1/00* (2006.01)

(52) U.S. Cl.
USPC ........................................... 604/319

(58) Field of Classification Search
USPC ........................ 604/313–319; 210/645–647
See application file for complete search history.

(56) References Cited

U.S. PATENT DOCUMENTS

| 452,131 | A | 5/1891 | Haughawout |
| 2,195,771 | A | 4/1940 | Estler |
| 2,305,289 | A | 12/1942 | Coburg |
| 2,524,750 | A | 10/1950 | Bellinger |
| 3,026,874 | A | 3/1962 | Stevens |
| 3,315,665 | A | 4/1967 | MacLeod |
| 3,568,675 | A | 3/1971 | Harvey |
| 3,604,421 | A | 9/1971 | Pizzella |
| 3,610,238 | A | 10/1971 | Rich, Jr. |
| 3,763,857 | A | 10/1973 | Schrading |
| RE29,319 | E | 7/1977 | Norbdy et al. |
| 4,082,092 | A | 4/1978 | Foster |
| 4,111,753 | A | 9/1978 | Folsom et al. |
| 4,153,055 | A | 5/1979 | Etes |
| 4,250,882 | A | 2/1981 | Adair |
| 4,469,092 | A | 9/1984 | Marshall et al. |
| 4,533,352 | A | 8/1985 | Van Beek et al. |
| 4,553,967 | A | 11/1985 | Ferguson et al. |
| 4,692,140 | A | 9/1987 | Olson |
| 4,735,603 | A | 4/1988 | Goodson et al. |
| 4,764,165 | A | 8/1988 | Reimels et al. |

(Continued)

FOREIGN PATENT DOCUMENTS

| WO | WO 89/11885 A1 | 12/1989 |
| WO | WO 99/53833 | 10/1999 |
| WO | WO 2009/066106 A1 | 5/2009 |

OTHER PUBLICATIONS

Mangram AJ, et al. "Special Articles: Guidelines for Prevention of Surgical Site Infection," *AJIC*, 27(2): 97-118 (Apr. 1999).

(Continued)

*Primary Examiner* — Loan H Thanh
*Assistant Examiner* — Nyca T Nguyen
(74) *Attorney, Agent, or Firm* — Bridget M. Hayden; Dorsey & Whitney LLP

(57) ABSTRACT

An apparatus for evacuating material from a surgical site, the apparatus including a housing and a filter media, and being operably coupled to a vacuum source. The housing includes a top surface, a bottom surface and an outer side wall, together defining an inner cavity of the housing. The housing further includes an access opening in fluid communication with the inner cavity and one or more ingress apertures in fluid communication with the access opening. The filter media is positioned in or adjacent to the inner cavity such that a flow of fluid through the ingress apertures is moved through the filter media.

28 Claims, 3 Drawing Sheets

(56) References Cited

U.S. PATENT DOCUMENTS

| | | | |
|---|---|---|---|
| 4,778,446 A | 10/1988 | Jensen | |
| 4,787,894 A | 11/1988 | Turnbull | |
| 4,795,435 A | 1/1989 | Steer | |
| 4,834,110 A | 5/1989 | Richard | |
| 4,921,492 A * | 5/1990 | Schultz et al. | 604/315 |
| 4,969,880 A | 11/1990 | Zamierowski | |
| 5,015,243 A * | 5/1991 | Schifano | 604/315 |
| 5,192,276 A | 3/1993 | Gatti | |
| 5,226,939 A | 7/1993 | Nicolas et al. | |
| 5,234,428 A | 8/1993 | Kaufman | |
| 5,279,599 A * | 1/1994 | Wilk | 604/317 |
| 5,312,296 A | 5/1994 | Aalto et al. | |
| 5,674,219 A | 10/1997 | Monson et al. | |
| 5,678,564 A | 10/1997 | Lawrence et al. | |
| 5,716,343 A * | 2/1998 | Kriesel et al. | 604/132 |
| 5,722,949 A | 3/1998 | Sanese | |
| 5,868,722 A | 2/1999 | Yeh et al. | |
| 5,941,873 A | 8/1999 | Korenfeld | |
| 6,055,987 A | 5/2000 | Griesbach et al. | |
| 6,071,267 A | 6/2000 | Zamierowski | |
| 6,110,259 A | 8/2000 | Schultz et al. | |
| 6,156,004 A | 12/2000 | Tremaine et al. | |
| 6,513,529 B1 | 2/2003 | Kamen | |
| 6,663,610 B1 * | 12/2003 | Thompson et al. | 604/313 |
| 6,942,650 B1 * | 9/2005 | Schultz et al. | 604/315 |
| 7,160,369 B2 * | 1/2007 | von Blucher et al. | 96/132 |
| 7,207,977 B2 * | 4/2007 | Thompson et al. | 604/313 |
| 7,400,383 B2 * | 7/2008 | Halbmaier et al. | 355/72 |
| 7,501,003 B2 * | 3/2009 | Muller et al. | 55/486 |
| 2010/0162895 A1 * | 7/2010 | Bohringer | 96/134 |
| 2010/0305524 A1 | 12/2010 | Vess et al. | |

OTHER PUBLICATIONS

Enggaard TP, et al. "Influence of Local Air Suction on the Density of Air-Borne Bacteria During Cementation of Alloplasties." *Ugeskr Laeger*, 159(7): 952-955, National Library of Medicine, www.ncbi.nlm.niyh.gov (Feb. 10, 1997).

Friberg, B. "Ultraclean Laminar Airflow Ors," *AORN J*, 67(4): 841-842, 845-851, National Library of Medicine, www.ncbi.nlm.nih.gov (Apr. 1998).

Friberg B, et al. "Zoned Vertical Ultraclean Operating Room Ventilation: A Novel Concept Making Long Side Walls Unnecessary," *Acta Orthop Scand.*, 67(6): 578-582, National Library of Medicine, www.ncbi.nlm.nih.gov (Dec. 1996).

Cornet, M. et al. "Efficacy of Prevention by High-Efficiency Particulate Air Filtration or Laminar Airflow Against *Aspergillus* Airborne Contamination During Hospital Renovation," *Infect. Control Hosp Epidemiol.*, 20(7): 508-513, National Library of Medicine, www.ncbi.nlm.nih.gov (Jul. 1999).

* cited by examiner

SYSTEMS AND METHODS FOR EVACUATING MATERIALS AT A SURGICAL SITE

FIELD OF THE INVENTION

This application relates to devices and systems for evacuating or removing surgical by-products from a surgical site and promoting cleanliness and/or sterility at a surgical site, and to methods of making and using such devices and systems. More particularly, the present application relates to systems, devices and methods for providing and/or maintaining a flow of ultra-clean, clean and/or sterile fluid at a surgical site as well as evacuating surgical byproducts from the surgical site.

BACKGROUND

Often times, during a surgical procedure, cutting, heating, and/or burning of tissue or other materials present at the surgical site generates unwanted byproducts such as, for example, smoke, particles, vapor, and/or plumes. Such byproducts can obscure the surgeon's field of vision and the odor generated is unpleasant and distracting to the surgical team and to the patient. Moreover, the surgical byproducts may contain infectious agents that present a danger to the patient as well as the surgical team, and can provide a lingering source of contamination within the operating area. Therefore, devices, systems and methods for effectively and efficiently removing such byproducts from a surgical site are desirable.

SUMMARY

In one embodiment, the present invention comprises an apparatus for evacuating material from a surgical site, the apparatus including a housing and a filter media, and being operably coupled to a vacuum source. The housing includes a top surface, a bottom surface and an outer side wall, together defining an inner cavity of the housing. The housing further includes an access opening in fluid communication with the inner cavity and one or more ingress apertures in fluid communication with the access opening. The filter media is positioned in or adjacent to the inner cavity such that a flow of fluid through the ingress apertures is moved through the filter media.

In one embodiment, the present invention comprises an evacuation apparatus and/or an evacuation system. The evacuation apparatus includes a housing and a filter media, and includes or is operably coupled to a vacuum device. The housing includes a top surface, a bottom surface spaced from the top surface, and an outer side wall extending at least partially between the top and bottom surfaces. The top surface, the bottom surface, and the outer sidewall define an inner cavity of the housing. The housing further includes an access opening extending between the top surface and the bottom surface, an inner facing being provided along a perimeter of the access opening. The inner cavity is in fluid communication with the access opening via the inner facing. The housing further includes one or more ingress apertures in fluid communication with the access opening. The filter media is positioned in the inner cavity such that a flow of fluid moved or drawn through the ingress apertures is forced, drawn and/or carried through the filter media. The vacuum device is in fluid communication with the inner cavity.

In one embodiment, the present invention comprises a method for evacuating surgical by-products from and promoting cleanliness and/or sterility at a surgical site. The method includes providing a evacuation head over a surgical site, providing a vacuum source, coupling the head and vacuum source, and actuating the vacuum source, thereby generating a flow of clean and/or sterile fluid across the surgical site and removing surgical byproducts from the surgical site. The evacuation head includes a housing and a filter media. The housing includes a top surface, a bottom surface spaced-apart from said top surface, and an outer side wall extending at least partially between said top and bottom surfaces. The top surface, the bottom surface, and the outer sidewall define an inner cavity of the housing. The housing further includes an access opening extending between the top surface and the bottom surface, an inner facing being provided along a perimeter of the access opening. The inner cavity is provided in fluid communication with the access opening via the inner facing. The housing further includes one or more ingress apertures in fluid communication with the access opening. The filter media is positioned in the inner cavity such that a flow of fluid drawn through the ingress apertures is forced, drawn or carried through the filter media.

It is to be understood that embodiments, including preferred embodiments, described in this application are for purposes of example and explanation and are not limiting. The accompanying drawings, which are incorporated in and constitute a part of the specification, illustrate exemplary embodiments.

DETAILED DESCRIPTION

Figure 1:
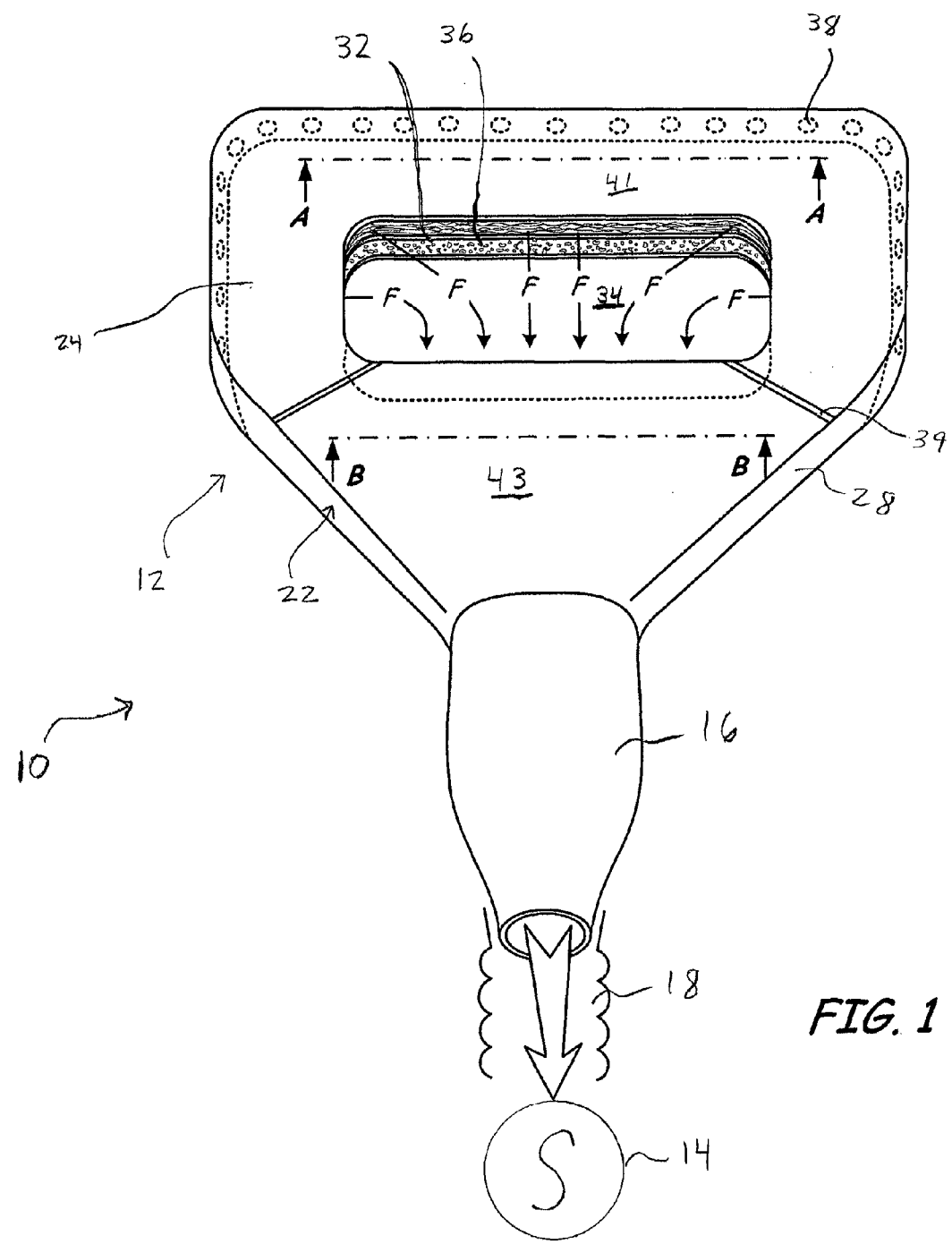
FIG. 1 is a top perspective view of an evacuation apparatus according to embodiments of the present application.

FIG. 1 is a perspective top view of a evacuation apparatus 10 in accordance with one embodiment of the present invention. The evacuation apparatus includes an evacuator head 12 in fluid communication with a negative pressure or vacuum source 14. The evacuator head 12 is in fluid communication with the vacuum source 14 via one or more fluid connecting members such as, for example, a nozzle member 16 and a fluid conduit 18. Generally, the evacuator head 12 may be positioned near a surgical site to create a flow of fluid across the surgical site, which acts both as a barrier to air-borne pathogens and contaminants as well as medium for surgical byproducts to be removed from the surgical site.

In illustrative embodiments, the evacuator head 12 may include a housing 22 having a top surface 24, a bottom surface 26, and an outer side wall 28 extending between an outer perimeter of the top and bottom surfaces 24, 26. Collectively, the top and bottom surfaces 24, 26 and outer side wall 28 may define an at least partially hollow space which may be thought of and/or referred to as an inner cavity 32. The housing 22 may further include one or more access openings 34 extending between the top and bottom surfaces 24, 26 to define an inner face 36 of the housing, and one or more ingress apertures 38 extending through the outer side wall 28 such that the ingress apertures 38 are in fluid communication with the inner cavity 32.

In some embodiments, the top and bottom surfaces 24, 26 may be provided as substantially planar surfaces. Alternatively, the surfaces 24, 26 may be provided with a contour and/or angle such that either or both of the surfaces 24, 26 generally conforms to a surface to which the evacuator head 12 is to be applied (e.g., to conform to the contours of a particular surgical site).

In various embodiments, the access opening 34 may be sized and shaped such that when the evacuation head 12 is positioned at a surgical site, at least a portion of the surgical site is positioned within the opening 34. In this regard, the opening 34 may have any size and shape suitable for the surgical site at which the evacuator head is to be used.

In some embodiments, at least a portion of the inner face 36 may be open such that the inner cavity 32 formed by the housing 22 is exposed. For example, as shown in FIG. 1, substantially the entire inner face 36 may be open to permit fluid flow therethrough. Alternatively, a portion of the inner face 26 may be covered by an inner wall portion that is integrally formed with the housing 22. The inner face 36 and/or the inner wall portion may extend substantially perpendicularly with respect to the top and bottom surfaces 24, 26, may be beveled/angled with respect to the top and bottom surfaces 24, 26, or be segmented such that it may be combinations thereof. In various embodiments, the configuration of the inner face 36 (e.g., presence of an inner wall, angle with respect to the top and bottom surfaces 24, 26) may be substantially the same as it extends around the access opening 34. Alternatively, the configuration may vary as it extends around the access opening 34.

In some embodiments, the housing 22 may be formed of a material that allows for the evacuator head 12 to generally conform to the shape of the surface to which it is applied. In this manner, the evacuator head may be adaptable to the contours of a variety of surgical sites. For example, the housing 22 may be formed of nonporous, pliable synthetic medical grade resin. Alternatively, the housing 22 may be formed of a fibrous material (e.g., cellulose or cotton fiber based material), an open-celled foam, a urethane film, a spun-lace polyester, a non-woven polyurethane tape, or the like. In further alternatives, the housing 22 may be formed of any known medical grade material.

In some illustrative embodiments, the housing 22 may be formed of a material having a pliability such that upon application of a negative pressure source to the inner cavity 32, the top and bottom walls 24, 26 may at least partially collapse, thereby at least partially obstructing flow through the inner cavity 32. Therefore, in some embodiments, one or more support layers may be provided within the inner cavity 32. Generally, the support layers may be constructed of materials that provide structure, firmness and/or rigidity to the housing 22 without substantially detracting from the flexibility of the evacuation head 12 and possess a porosity that both permits the flow of surgical site byproducts (e.g., exhaust, smoke, particles, vapor, plumes) and prevents the ingress of larger materials such as tissue and surgical instruments. For example, one or more of the support layers may be formed from foam urethane, or other suitable reticulated, open-cell foam material, a supporting matrix, or the like. In further alternatives, the support layers may be formed of a synthetic or natural material that is hydrophobic such that it resists absorption of fluids often present at surgical sites. In one embodiment, the support layers may be formed of a reticulated open cell foam having between about 5 and about 40 pores per inch (ppi). In another embodiment, the support layers may be provided with a plurality or matrix of shafts or channels to facilitate flow therethrough.

In various embodiments, including some preferred embodiments, one or more partitions 39 may be provided in the inner cavity 32 for directing the flow of fluid, e.g. ambient air, drawn into the inner cavity 32, to a particular segment of the access opening 34 for discharge. As shown in FIG. 1, a pair of partitions 39 may be provided in the inner cavity 32 such that the inner cavity 32 is separated into an ingress flow region 41 and an egress flow region 43. The partitions 39 may be impermeable or semi-impermeable, and may extend in height between the top and the bottom surfaces 24, 26 of the housing 22, and in length between the outer sidewall 28 and the perimeter of the access opening 34. The partitions 39 may be formed as discrete members or may be integrally formed with the housing 22. While only two partitions 39 are depicted in FIG. 1, any number of partitions 39 may be included. In an alternative embodiment, the partitions 39 may be omitted.

In some embodiments, the partitions 39 may be positioned within the inner cavity 32 such that ingress of flow to the access opening 34 extends around a selected portion of the perimeter of the access opening 34 (the "ingress portion"), which is generally opposite the nozzle member 16. In this manner, the partitions 39 may concentrate and/or direct the flow to a selected portion of the access opening 34. In one embodiment, the ingress portion may encompass about 45 to about 270 degrees of the perimeter of the access opening 34. Alternatively, the ingress portion may encompass any portion of the perimeter less than approximately 330 degrees. In an alternative embodiment, three or more partitions 39 may be provided to form a manifold-type system that separates the ingress flow into lanes or channels so that a consistent flow velocity may be achieved across the ingress portion of the access opening 34. It is to be appreciated that with or without the partitions 39, a portion of the ingress flow may be diverted around the access opening 34, effectively flowing around the surgical site.

In various embodiments, one or more filter media layers may be provided in the inner cavity 32. Generally, the filter media layers may be arranged in the cavity 32 such that the fluid traveling through the fluid ingress region 41 passes through the filter media layers prior to being discharged into and across the access opening 34. In this manner, fluid traveling across the opening 34, and thus the surgical site, may be substantially ultra-clean, clean and/or sterile. The filter media layers may be formed from any material suitable for removing pathogens, particles and/or contaminants from fluid drawn into the evacuation head 12 through the ingress apertures 38. In one embodiment, one or more filter media layers may be formed from a ultra low penetration air (ULPA) material that entraps and contains particulate matter having a size of about 0.12 microns or greater at an efficiency of about 99.999%. As will be discussed in further detail below, in various embodiments, the filter media layers and the support layers may be layered or stacked relative to one another in one or more layering arrangements and/or thicknesses and/or segments.

In some embodiments, the housing 22 may include a plurality of ingress apertures 38 extending through the top surface 24, the side wall 28, or combinations thereof. Generally, the ingress apertures 38 may serve as an entrance point for fluid, including ambient air, to flow into the inner cavity 32 of the evacuator head 12, particularly, the fluid ingress region 41. The ingress apertures 38 may be in the form of pinholes, elongated openings, or strips, or any other shape suitable for permitting the entry of a selected volume and/or rate of fluid into the fluid ingress region 41. As shown, in one embodiment, ingress apertures 38, in the form of pinholes, may be provided on a portion of the outer side wall 28 that surrounds the ingress region 41. Additionally, or alternatively, ingress apertures 38 may be provided on a portion of the top surface 24 that overlies the ingress region 41. As will be discussed in further detail below, in some embodiments, the ingress apertures 38 may be positioned relative to the filter media layers such that fluid drawn therethrough is passed through the filter media prior to being discharged into the access opening 34. In this manner, fluid entering through the ingress apertures 38 may be cleaned and/or sterilized prior to being passed over a surgical site.

In some illustrative embodiments, the support layers and filter media layers may be provided in one or more layering arrangements within the evacuator head 12. For example, a first layering arrangement may provided in the fluid ingress region 41 of the inner cavity 32 and a second layering arrangement may provided in the fluid egress region 43 of the inner cavity 32.

Figure 1A:
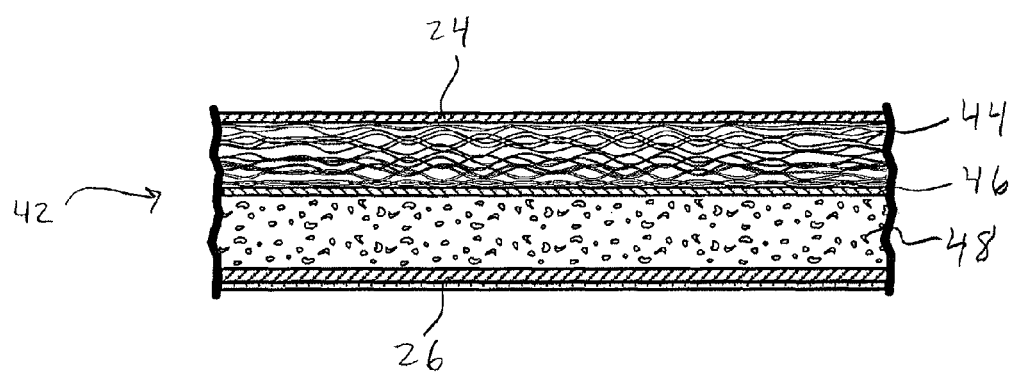
FIG. 1a is a cross-sectional view of the evacuation apparatus of FIG. 1 taken along line A-A.

In accordance with some embodiments of the present invention, FIG. 1A depicts a cross sectional view of the evacuator head 12 of FIG. 1, particularly, the fluid ingress region 41, taken along line A-A. As shown, a first layering arrangement 42 may include a filter media layer 44 positioned in overlying relation with respect to an impervious layer 46, the impervious layer 46 positioned in overlying relation with respect to a support layer 48. Alternatively, the positions of the filter media layer 44 and the support layer 48 in FIG. 1A may be reversed (i.e., the support layer 48 may be positioned over the filter media layer 44). Suitable impervious layers 46 may be formed of a material that substantially prevents the transmission of fluid between the filter media and support layers 44, 48. In this manner, the flow of fluid through ingress fluid region 41 is prevented from diversion into the support layer 48 before being discharged into the access opening 34, which could affect the degree of cleanliness and/or sterility of the ingress flow. Collectively, the layers 44, 46, and 48 may have a thickness which substantially corresponds to the gap between the top and bottom surfaces 24, 26 in the fluid ingress region 41 (i.e., the layering arrangement 42 may substantially fill the fluid ingress region 41 of the inner cavity 32.

In an alternative embodiment, the first layering arrangement 42 may include a pair of filter media layers 44 that "sandwich" a support layer 48, and that are separated from the support layer by respective impervious layers. In a further alternative, the filter media layer 44 itself may formed as a plurality of layers. In yet another alternative, the first layering arrangement 42 may include one or more filter media layers 44, without an impervious layer 46 and/or a support layer 48.

In illustrative embodiments, the ingress apertures 38 may be positioned relative to the first layering arrangement 42 such that fluid drawn therethrough is passed through the filter media layer 44 prior to being discharged across the access opening 34. For example, the ingress apertures 38 may be provided on the outer side wall 28 of the fluid ingress region at a height that corresponds to the position of the filter media layer 44 within the inner cavity 32. Alternatively, the ingress apertures 38 may be provided on a portion of the top surface 24 that is immediately above the filter medial layer 44. In such embodiments, fluid ingress pathways may be defined by the pathways traveled by the ambient fluid as it passes into the ingress apertures 38 and through the filter media layer 44 before being discharged into the access opening 34.

Figure 1B:
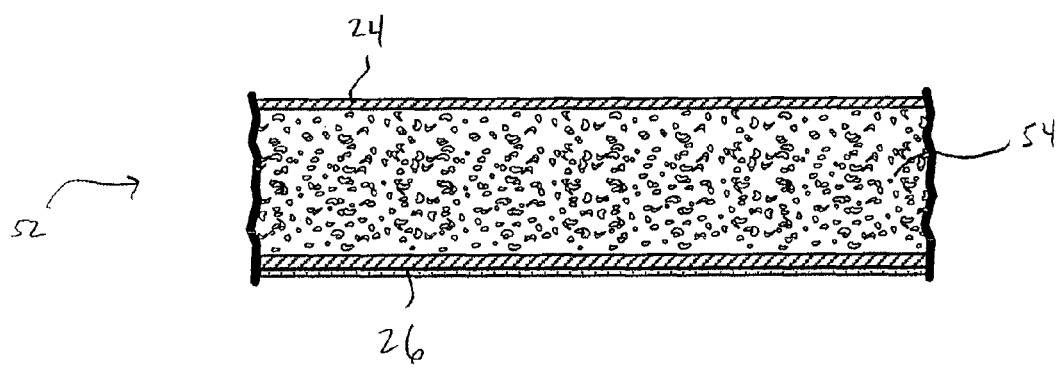
FIG. 1b is a cross-sectional view of the evacuation apparatus of FIG. 1 taken along line B-B.

FIG. 1B depicts a cross sectional view of the evacuator head 12 of FIG. 1, particularly, the fluid egress region 43, taken along line B-B. As shown, a second layering arrangement 52 may include one or more support layers 54 that, collectively, have a thickness that substantially corresponds to the gap between the top and bottom surfaces 24, 26 in the fluid egress region 43. In an alternative embodiment, the second layering arrangement may also include a filter media layer, or a combination of filter media and support layers, with or without impervious layers.

With respect to the layers of the first and second layering arrangements 42, 52, the thickness of the layer or layers may be uniform, or may vary. Likewise, the thickness of an individual layer may vary across its width or length. For example, a layer or a portion thereof may have or include a graded or graduated thickness across at least a portion thereof. The one or more layers may be provided in a contiguous relationship, that is directly on top of or adjacent to another layer of the arrangement 42 or 52.

In various embodiments, including some preferred embodiments, the fluid ingress region 41 and the fluid egress region 43 may be provided in fluid communication with the vacuum source 14. For example, as shown in FIG. 1, the nozzle 16 may be coupled to an opening in a portion of the housing 22 that surrounds the egress fluid region 43 and is generally opposite the ingress fluid region 41. Alternatively, the nozzle 16 may extend through the housing 22 and into the egress fluid region 43. Through this fluid communication, a negative pressure generated by the vacuum source 14 may cause fluid to be drawn from within the access opening 34 into the fluid egress region 43. Pulling of fluid from within the accessing opening 34 in this manner may, in turn, induce a flow of fluid through the ingress region 41, via the ingress apertures, and into the access opening 34, via the inner facing 36. The resulting flow of fluid across the access opening 34 and, thus, a surgical site, is shown generally by arrows F in FIG. 1.

Figure 2:
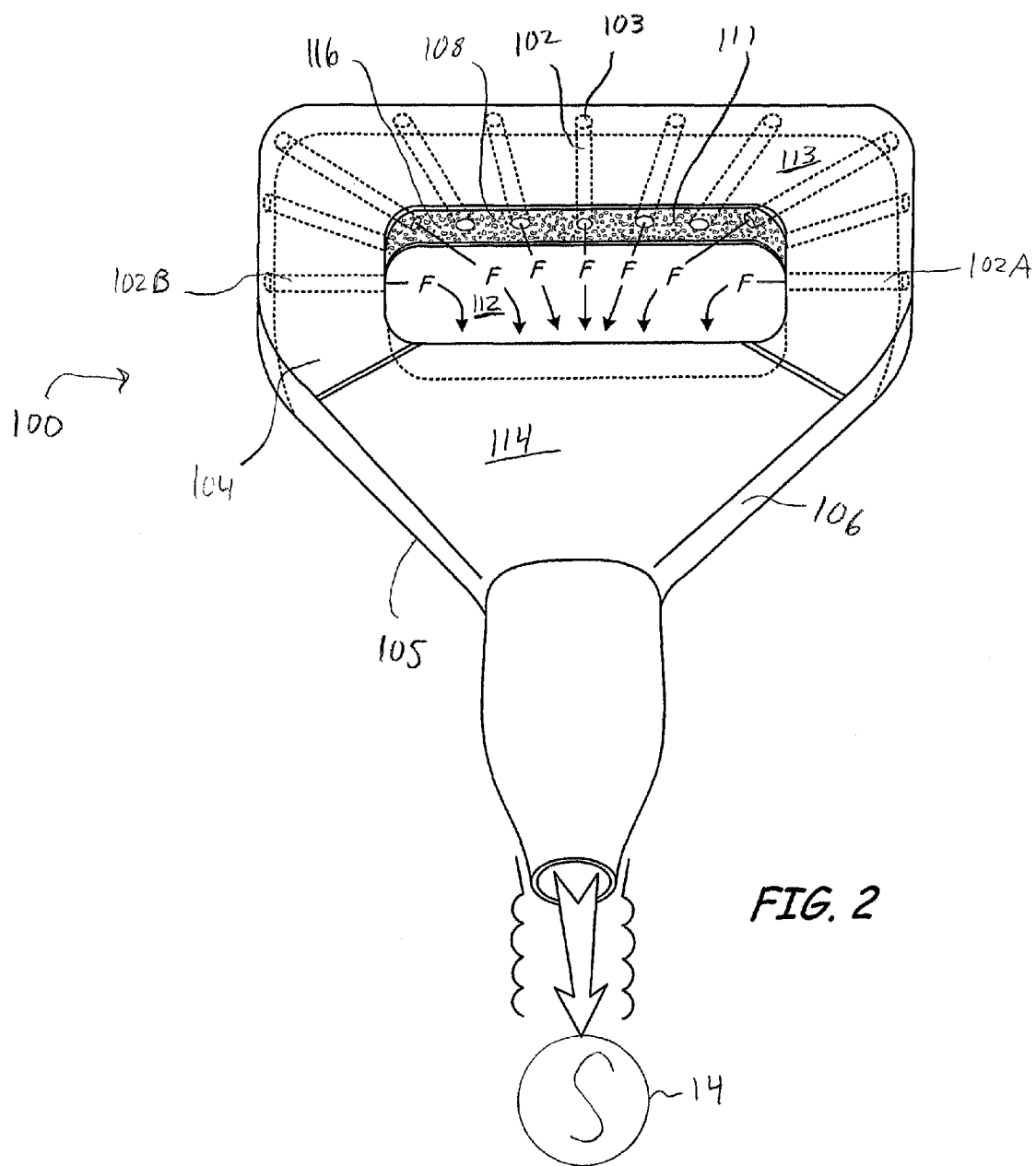
FIG. 2 is a top perspective view of an evacuation apparatus according to embodiments of the present application.

Referring now to FIG. 2, a perspective top view of an evacuation apparatus 100 in accordance with another embodiment is shown. For purposes of brevity, only differences between the evacuation apparatus 100 and previously described exemplary embodiments are discussed herein.

As shown in FIG. 2, the evacuation apparatus 100 may include a plurality of discrete ingress pathways or ingress cartridges 102 that extend from ingress apertures 103 provided in any or all of a top surface 104, a bottom surface 105, and an outer side wall 106, into an inner cavity 108, before terminating at an inner face 111 of an access opening 112. As with the ingress apertures 38, the ingress apertures 103 and ingress cartridges 102 may serve as an entrance point for fluid, including ambient air, into a fluid ingress region 113 of the inner cavity 108. The ingress cartridges 102 may be formed from a substantially impermeable material. In this manner, fluid passing through the cartridges 102 may not pass through the cartridge wall into the inner cavity 108. The ingress cartridges 102 may be provided in spaced relation around the perimeter of the access opening 112. In this regard, the position of the two "end" ingress cartridges 102 (labeled cartridges 102A and 102B in FIG. 2) may define the boundaries of the fluid ingress region 113 and a fluid egress region 114.

In some embodiments, any or all of the ingress cartridges 102 may be at least partially filled or packed with a filter media. The filter media may be provided in the cartridges 102 such that a fluid stream passing through the cartridges 102 is forced, drawn or carried through the filter media. The filter media may be formed of the same material described with respect to the filter media of previous embodiments.

In various embodiments, the inner cavity 108 may include one or more support layers 116. For example, the support layers 116 may substantially fill the portion of the inner cavity 108 that is not taken up by the ingress cartridges 102. In this regard, the cartridges 102 may extend through the support layers 116 and/or be provided above or below the support layers 116. The support layers 116 may be formed of the same material described with respect to the support layers of previous embodiments.

In some embodiments, the evacuation apparatus of the present invention may be used as a stand-alone device. In alternative embodiments, the evacuation apparatus may be integrated into another surgical device, such as a surgical drape comprising a flexible, cloth-like sheet material. Such drapes may be used to establish, define or set off a surgical field.

In use, the evacuation apparatus 10 or 100 may be detachably affixed to the skin surrounding a surgical site such as by a suitable adhesive layer that may contact, be applied to, or carried by the bottom surface 26 of the housing 22. In this manner, the evacuation head 12 of the apparatus 10 may form a substantially complete, airtight seal of the bottom surface 26 against the skin or any skin covering (such as a drape). Upon actuation of the vacuum source 14, a flow of fluid may be drawn into the ingress region 41 of the inner cavity 32, via the ingress openings and/or pathways, into a filter media. As the fluid is transported through the filter media, pathogens and/or contaminants from the fluid may be removed, thereby creating a flow of clean, ultra-clean and/or sterile fluid. Subsequently, the flow of clean and/or sterile fluid may be discharged, through the inner face 36, into the access opening 34. Under the force of the vacuum source 14, the clean and/or sterile flow may be drawn across the access opening 34, through an opposite side inner face 36 and into the egress region 43. The effect of this flow may be two-fold: it may act as a ultra-clean, clean and/or sterile barrier to air-borne pathogens and contaminants, and it may entrain surgical byproducts (e.g., smoke, particles, vapor, plumes) thereby removing such products from the surgical site. The flow may then be transferred across the fluid egress region before being drawn into the vacuum source 14 via the nozzle member 16 and conduit 18. The vacuum source 14 may pass or draw the flow through a filtering material before discharging it into the surgical environment. It is to be appreciated that the evacuation apparatus 100 may be used in a substantially similar manner.

It is to be appreciated that during use, because one end of the access opening 34 is open to the surgical environment, in addition to drawing fluid into the access opening 34 via the ingress apertures, the vacuum source 14 may draw ambient fluid into the access opening 34 via the open end of the access opening 34. That is, it is to be appreciated that the flow of fluid across the access opening 34 may be a mixture of ultra-clean, clean and/or sterile air that was drawn through the fluid ingress region 41 and ambient fluid that was drawn through the open end of the access opening 34. It is to be further appreciated that the ratio of ultra-clean, clean and/or sterile fluid to ambient fluid in the flow across the access opening 34 may be varied or manipulated by varying one or more aspects of the evacuation head 12 and/or the vacuum source 14. For example, any or all of the number and size of the ingress apertures or ingress pathways, filter material, packing density of filter material, size and shape of the inner facing, size and shape of the access opening, and/or strength of the vacuum source may be selected, varied or manipulated to achieve a desired ratio of ultra-clean, clean and/or sterile fluid to ambient fluid. The evacuation head 12 and vacuum source 14 may be configured such that flow rates of between about 5 cubic feet per minute ("cfm") and 65 cfm, according to one embodiment, and between about 20 cfm and about 30 cfm, according to another embodiment, may be achieved across the access opening 34. Additionally, the flow across the opening may be at a steady rate, a variable rate, or a pulsed rate.

With regard to fastening, mounting, attaching or connecting the components to form embodiments of the device and/or system as a whole, unless specifically described otherwise, conventional fasteners such as machine screws, nut and bolt connectors, machine threaded connectors, snap rings, hose clamps such as screw clamps and the like, rivets, nuts and bolts, toggles, pins and the like may be used. Components may also be connected by adhesives, glues, heat sealing, snap fitting, welding, ultrasonic welding, and friction fitting or deformation, if appropriate. Unless specifically otherwise disclosed or taught, materials for making components may be selected from appropriate materials such as metal, metallic alloys, natural and manmade fibers, vinyls, plastics and the like, and appropriate manufacturing or production methods including casting, extruding, molding and machining may be used.

While the present invention has been described with reference to various embodiments, including some preferred embodiments, it will be understood that these embodiments are illustrative and that the scope of the invention is not limited to them. Many variations, modifications, additions, and improvements are possible. Also, any functionality may be separated or combined differently in various embodiments of the invention or described with different terminology. These and other variations, modifications, additions, and improvements are to be considered as within the scope of the invention as defined in the claims that follow.

The invention claimed is:

1. An evacuation apparatus comprising:
    a housing comprising:
        a top surface, a bottom surface spaced from said top surface, and an outer side wall extending at least partially between said top and bottom surfaces, wherein the top surface, the bottom surface and the outer sidewall define an inner cavity of the housing;
        an access opening extending between the top surface and the bottom surface, an inner facing being provided along a perimeter of the access opening, wherein the inner cavity is provided in fluid communication with the access opening via the inner facing;
        a support material positioned in at least one of adjacent to or in the inner cavity such that the support material resists collapse of the housing;
        one or more ingress apertures in fluid communication with the access opening, wherein one or more of the ingress apertures are formed in the outer sidewall; and
    a filter media positioned in at least one of adjacent to or in the inner cavity and distinct from and outside of the support material such that a flow of fluid through the ingress apertures moves through the filter media; and
    a vacuum device in fluid communication with the inner cavity.

2. The evacuation apparatus of claim 1, wherein at least a portion of the filter media and at least a portion of the support material are provided in a layering arrangement comprising a filter media layer overlaying or being overlaid by a support material layer.

3. The evacuation apparatus of claim 2, wherein the inner cavity comprises a fluid egress region adjacent the vacuum source and an fluid ingress region opposite the fluid egress region, and wherein the fluid ingress region encompasses about 45 to about 270 degrees of a perimeter of the access opening.

4. The evacuation apparatus of claim 3 wherein the layering arrangement is provided in the fluid ingress region.

5. The evacuation apparatus of claim 4, wherein the support material is provided in the fluid egress region.

6. The evacuation apparatus of claim 2, wherein the layering arrangement further comprises an essentially gas-impermeable layer positioned between the filter media layer and the support material layer.

7. The evacuation apparatus of claim 6, wherein the ingress apertures are provided to the outer side wall and at a height on the outer side wall that corresponds to a position of the filter media layer within the inner cavity.

8. The evacuation apparatus of claim 1, wherein the filter media comprises cartridges extending between one or more of the ingress apertures and the inner facing.

9. The evacuation apparatus of claim 8, wherein the cartridges comprise cartridge walls formed of an essentially gas-impermeable material.

10. The evacuation apparatus of claim 8, wherein the filter media comprises an ULPA material.

11. The evacuation apparatus of claim 1, wherein the filter media comprises an ULPA material.

12. The evacuation apparatus of claim 1, wherein the support material is positioned in the inner cavity.

13. The evacuation apparatus of claim 1, wherein the bottom surface of said housing includes an adhesive layer for adhesive attachment of said apparatus at a surgical site.

14. An evacuation apparatus comprising:
a housing comprising:
a top surface, a bottom surface spaced from said top surface, and an outer side wall extending at least partially between said top and bottom surfaces, wherein the top surface, the bottom surface and the outer sidewall define an inner cavity of the housing;
an access opening extending between the top surface and the bottom surface, an inner facing being provided along a perimeter of the access opening, wherein the inner cavity is provided in fluid communication with the access opening via the inner facing;
a support material positioned in at least one of adjacent to or in the inner cavity such that the support material resists collapse of the housing, wherein the support material is a generally porous material;
one or more ingress apertures in fluid communication with the access opening, wherein one or more of the ingress apertures are formed in the outer sidewall; and
a filter media positioned in at least one of adjacent to or in the inner cavity and distinct from and outside of the support material such that a flow of fluid through the ingress apertures moves through the filter media; and
a vacuum device in fluid communication with the inner cavity.

15. The evacuation apparatus of claim 14, wherein at least a portion of the filter media and at least a portion of the support material are provided in a layering arrangement comprising a filter media layer overlaying or being overlaid by a support material layer.

16. The evacuation apparatus of claim 15, wherein the layering arrangement further comprises an essentially gas-impermeable layer positioned between the filter media layer and the support material layer.

17. The evacuation apparatus of claim 16, wherein the ingress apertures are provided to the outer side wall and at a height on the outer side wall that corresponds to a position of the filter media layer within the inner cavity.

18. The evacuation apparatus of claim 15, wherein the inner cavity comprises a fluid egress region adjacent the vacuum source and an fluid ingress region opposite the fluid egress region, and wherein the fluid ingress region encompasses about 45 to about 270 degrees of a perimeter of the access opening.

19. The evacuation apparatus of claim 18, wherein the layering arrangement is provided in the fluid ingress region.

20. The evacuation apparatus of claim 19, wherein the support material is provided in the fluid egress region.

21. The evacuation apparatus of claim 14, wherein the filter media comprises cartridges extending between one or more of the ingress apertures and the inner facing.

22. The evacuation apparatus of claim 21, wherein the cartridges comprise cartridge walls that are formed of an essentially gas-impermeable material.

23. The evacuation apparatus of claim 21, wherein the filter media comprises an ULPA material.

24. The evacuation apparatus of claim 14, wherein the filter media comprises an ULPA material.

25. The evacuation apparatus of claim 14, a wherein the support material is positioned in the inner cavity.

26. The evacuation apparatus of claim 14, wherein the bottom surface of said housing includes an adhesive layer for adhesive attachment of said apparatus at a surgical site.

27. A method for promoting cleanliness and/or sterility at a surgical site, the method comprising the steps of;
positioning an evacuation head adjacent to the surgical site, wherein said evacuation head comprises:
a housing comprising:
a top surface, a bottom surface spaced from said top surface, and an outer side wall extending at least partially between said top and bottom surfaces, wherein the top surface, the bottom surface and the outer sidewall define an inner cavity of the housing;
an access opening extending between the top surface and the bottom surface, an inner facing being provided along a perimeter of the access opening, wherein the inner cavity is in fluid communication with the access opening via the inner facing;
a support material positioned in at least one of adjacent to or in the inner cavity such that the support material resists collapse of the housing;
one or more ingress apertures in fluid communication with the access opening, wherein one or more of the ingress apertures are formed in the outer sidewall; and
a filter media positioned in the inner cavity and distinct from and outside of the support material such that a flow of fluid drawn through the ingress apertures is moved through the filter media;
providing a vacuum source;
coupling said evacuation head and said vacuum source; and
actuating said vacuum source, thereby generating a flow of clean and/or sterile fluid across the surgical site and removing surgical byproducts from the surgical site.

28. A method for promoting cleanliness and/or sterility at a surgical site, the method comprising the steps of;
positioning an evacuation head adjacent to the surgical site, wherein said evacuation head comprises:
a housing comprising:
a top surface, a bottom surface spaced from said top surface, and an outer side wall extending at least partially between said top and bottom surfaces, wherein the top surface, the bottom surface and the outer sidewall define an inner cavity of the housing;
an access opening extending between the top surface and the bottom surface, an inner facing being provided along a perimeter of the access opening, wherein the inner cavity is in fluid communication with the access opening via the inner facing;

a support material positioned in at least one of adjacent to or in the inner cavity such that the support material resists collapse of the housing, wherein the support material is a generally porous material;

one or more ingress apertures in fluid communication with the access opening, wherein one or more of the ingress apertures are formed in the outer sidewall; and a filter media positioned in the inner cavity and distinct from and outside of the support material such that a flow of fluid drawn through the ingress apertures is moved through the filter media;

providing a vacuum source;

coupling said evacuation head and said vacuum source; and actuating said vacuum source, thereby generating a flow of clean and/or sterile fluid across the surgical site and removing surgical byproducts from the surgical site.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,708,985 B2 | |
| APPLICATION NO. | : 13/091213 | |
| DATED | : April 29, 2014 | |
| INVENTOR(S) | : Leonard S. Schultz | |

It is certified that error appears in the above-identified patent and that said Letters Patent is hereby corrected as shown below:

Specification

| Column | Line | PTO | Should Be |
|---|---|---|---|
| 4 | 4 | "into the inner cavity 32, to a particular" | — into the inner cavity 32 to a particular — |

Claims

| Column | Line | PTO | Should Be |
|---|---|---|---|
| 10 | 19 | "apparatus of claim 14, a wherein the" | — apparatus of claim 14, wherein the — |

Signed and Sealed this
Eighth Day of July, 2014

Michelle K. Lee
*Deputy Director of the United States Patent and Trademark Office*